United States Patent [19]

Shea

[11] Patent Number: 5,514,182
[45] Date of Patent: May 7, 1996

[54] PROSTHETIC JOINT WITH SEMIPERMEABLE CAPSULE WITH REINFORCING RIBS

[75] Inventor: Kevin G. Shea, Salt Lake City, Utah

[73] Assignee: University of Utah, Salt Lake, Utah

[21] Appl. No.: 241,357

[22] Filed: May 11, 1994

Related U.S. Application Data

[63] Continuation-in-part of Ser. No. 107,940, Aug. 17, 1993, abandoned.

[51] Int. Cl.⁶ .................................. A61F 2/30; A61F 2/34
[52] U.S. Cl. .................................. 623/18; 623/16; 623/22; 623/23
[58] Field of Search .................................. 623/16, 18, 19, 623/22, 23; 403/50

[56] References Cited

U.S. PATENT DOCUMENTS

| | | | |
|---|---|---|---|
| Re. 33,701 | 9/1991 | Triquet | 403/50 |
| 184,461 | 11/1876 | Cooper | 403/50 |
| 3,648,294 | 3/1972 | Shahrestani | 623/22 |
| 3,683,421 | 8/1972 | Martinie | 623/23 |
| 3,739,403 | 6/1973 | Nicolle | 623/21 |
| 3,864,758 | 2/1975 | Yakich | 623/22 |
| 3,869,730 | 3/1975 | Skobel | 623/19 |
| 4,731,088 | 3/1988 | Collier | 623/22 |
| 5,217,493 | 6/1993 | Raad et al. | 623/11 |

FOREIGN PATENT DOCUMENTS

| | | | |
|---|---|---|---|
| 0346294 | 12/1989 | European Pat. Off. | 623/22 |
| 1533684 | 12/1989 | U.S.S.R. | 623/22 |

*Primary Examiner*—David Isabella
*Attorney, Agent, or Firm*—Kelly Bauersfeld & Lowry

[57] ABSTRACT

A prosthetic joint such as a hip prosthesis includes a semipermeable membrane to encapsulate articulating surfaces of the joint. The semipermeable membrane permits circulation of natural body fluid to the articulating surfaces of the joint for lubrication purposes, while preventing systemic distribution of particulate generated at the articulating surfaces in the course of normal mechanical wear. In addition, the membrane isolates the articulating surfaces from other particulate debris, such as fragments of bone cement and/or bone ingrowth materials associated with the prosthesis-bone interface. One or more stay rings are carried by the membrane to prevent the membrane from becoming entrapped between articulatory surfaces of the prosthetic joint.

19 Claims, 3 Drawing Sheets

PROSTHETIC JOINT WITH SEMIPERMEABLE CAPSULE WITH REINFORCING RIBS

This is a continuation-in-part of U.S. Ser. No. 08/107,940, filed Aug. 17, 1993 now abandoned.

BACKGROUND OF THE INVENTION

This invention relates generally to improvements in prosthetic joints such as hip prostheses and the like. More specifically, this invention relates to an improved prosthetic joint wherein articulating surfaces are encapsulated within a semipermeable membrane which prevents undesired migratory distribution of prosthesis-related particulate while permitting natural fluid circulation for prosthesis lubrication.

Artificial or prosthetic devices for implantation into animals, particularly humans, have been the subject of extensive research and development efforts for many years. Such prosthetic devices have typically comprised one or more implant components formed from a relatively biostable material or materials having selected structural properties and unique shapes to replace all or part of selected bone structures, such as an anatomical joint including, for example, hip joints, knee joints, shoulder joints, etc. The implant components are installed by surgical access to the subject bone or joint region, and by resection of one or more bone surfaces to accommodate direct implant component attachment to the bone.

More specifically, in the example of a hip prosthesis, the hip joint of a patient is accessed surgically to permit removal of the head and neck of the patient's femur to expose the internal medullary canal. A prosthetic component having an artificial femoral head and neck is then implanted by seating an elongated stem of the prosthesis component into the medullary canal. In many procedures, a second prosthetic component is implanted into the patient's acetabulum and includes a typically plastic bearing cup to engage the head of the femoral component and thereby form a reconstructed artificial hip joint. In the past, the femoral and/or acetabular prosthetic components have been secured to adjacent patient bone by use of a bone cement, such as methylmethacrylate. In other prosthesis design, porous bone ingrowth coatings have been provided on the prosthetic components for non-cemented fixation to patient bone by ingrowth and/or resorption of patient bone and/or tissue.

During normal post-surgical patient ambulation, it is known that a substantial quantity of microscopic and macroscopic particulate debris is generated by the prosthetic joint. More specifically, such particulate debris is produced at articulating surfaces of the joint. By way of example, in a hip prosthesis, the articulating surfaces defined by the femoral head formed typically of a cobalt-chrome or titanium alloy which mates with the plastic acetabular bearing cup produces a substantial quantity of plastic-based particles in the course of normal mechanical wear. These particles can be distributed systemically, and the long term toxicity and oncogenic properties of such particles are unknown.

In addition, localized distribution of particulate contributes to osteolysis or direct bone resorption around the prosthesis, leading to loosening, pain and eventual failure of the prosthesis. Revision surgery for a failed prosthesis is more difficult, more costly, and potentially involves greater risk of complications.

In addition, particulate debris can be generated at the prosthesis-bone interface. This type of particulate can include bone cement fragments and/or small ceramic-based or metal-based debris from porous bone ingrowth materials. Prosthesis-related particles of these types are typically relatively large in size and significantly harder than the plastic bearing materials used at articulating surfaces of the prosthetic joint. Accordingly, circulation of particulate debris from the prosthesis-bone interface to the articulating surfaces of the joint can contribute to significant increases in wear rate.

The above-discussed problems of prosthesis-related particulate debris have resulted in attempts to encapsulate the articulating surfaces of the prosthetic joint. In one approach, as disclosed in U.S. Pat. No. 3,683,421, the articulating joint surfaces are contained within a bellows-like seal to define a closed pocket for containing a synthetic lubricant used to lubricate the articulating surfaces. Unfortunately, however, a satisfactory lubricant for this purpose has not been available or otherwise approved for human implantation. In an alternative design approach as described in U.S. Pat. No. 3,739,403, the articulating joint surfaces are contained within a ball-shaped shell having small ports to permit circulation of natural body fluids past the articulating surfaces for lubrication. The encapsulating shell is intended to prevent ingrowth of large body tissues into the region of the articulating surfaces. Particulate circulation to or from the articulating surfaces, however, is not prevented.

In other joint capsule designs, a semipermeable membrane has been proposed for use in capturing prosthesis-related particulate debris, yet still allow for natural circulation of body fluids to the joint. See, for example, U.S. Pat. Nos. 4,731,088 and 4,822,368, as well as European Patent 0,346,294. These designs, however, use bent wires or drawstrings to hold a fabric-based membrane in place. Such membrane attachment structures must be subjected to significant tension in order to provide an effective particulate seal, but high tension forces increase the risk of membrane rupture at the point of attachment and also increase the risk of failure of the attachment device. If the attachment device comes loose, it can become trapped at the articulatory surfaces to cause dislocation in some cases. Moreover, in these devices, the fabric-based membrane is loosely mounted about the prosthetic joint so that the membrane can also be pinched between articulatory surfaces to result in membrane rupture and possible joint dislocation.

There exists, therefore, a need for further improvements in prosthetic joints of the type intended for human implantation, wherein undesired circulation of prosthesis-related particulate to or from articulating surfaces of the joint is substantially prevented by a semipermeable membrane which permits circulation of natural body fluids to those articulating surfaces for purposes of lubrication, while safeguarding the membrane against significant risk of failure and/or entrapment between articulating surfaces. The present invention fulfills these needs and provides further related advantages.

SUMMARY OF THE INVENTION

In accordance with the invention, an improved prosthetic joint such as a hip prosthesis or the like is provided for implantation into a patient. The prosthetic joint comprises a pair of prosthetic components adapted for secure fixation to adjacent patient bones and defining articulating joint motion surfaces which a accommodate substantially normal post-surgical range of joint motion. A semipermeable membrane is connected between the two prosthetic components and encapsulates the articulating surfaces. The semipermeable membrane permits circulation of natural body fluids past the articulating surfaces for lubrication. However, the semipermeable membrane prevents systemic distribution of particulate debris generated at the articulating surfaces, while additionally isolating the articulating surfaces from contact with other particulate debris associated with the interface between the prosthetic components and patient bone. At least one and preferably a plurality of stay rings are secured to the membrane to prevent the membrane from being entrapped between the articulating surfaces of the prosthetic joint.

In one preferred form of the invention, the prosthetic joint comprises a hip prosthesis including a femoral component and an acetabular component. The femoral component is formed from a biocompatiable high strength material, such as cobalt-chrome or titanium alloy, to have an elongated stem with a size and shape for secure fixation into the medullary canal of a resected patient femur. An upper region of the femoral stem is enlarged and contoured to correspond generally with the medullary canal shape, and is joined to an upwardly extending neck adapted to carry a generally spherical or ball-shaped femoral head. The acetabular component comprises a cup-shaped shell formed from a similar high strength and biocompatible alloy material for implantation into a prepared patient acetabulum. A cup-shaped bearing liner formed typically from a high density plastic is seated within the acetabular shell and defines an open socket for articulatory reception of the ball-shaped head on the femoral component.

The semipermeable membrane comprises a flexible and biocompatible fabric sheath formed in an annular or cylindrical configuration to surround the articulatory interface between the femoral and acetabular components. Opposite ends of the annular membrane are securely attached to the femoral and acetabular components, whereby the membrane surrounds and encapsulates the articulatory surfaces of the prosthetic joint. A preferred membrane material is expanded polytetrafluoroethylene (ePTFE) marketed for example, by W. L. Gore & Associates of Newark, Del. under the trademark GORE-TEX. In use, the semipermeable membrane permits natural body fluid circulation to the articulatory surfaces, while preventing migration of particulate debris to or from the articulating surfaces.

The stay rings are secured to the membrane at positions along the length of the membrane selected to prevent any portion of the membrane from flexing to a position interfering with joint motion. The stay rings thus prevent membrane failure and/or joint dislocation as a result of the membrane being pinched between the joint surfaces.

The opposite ends of the cylindrical membrane are respectively secured to a pair of mounting collars adapted for secure attachment to the femoral and acetabular components of the prosthesis. In the preferred form, the mounting collars are threadably attached to the femoral and acetabular components to permit easy mounting and removal during surgical implantation. Each mounting collar also includes at least one set screw or similar lock device for preventing inadvertent removal of the mounting collars after final implantation position is achieved. Seal ring gaskets prevent leakage between the mounting collars of the respective femoral and acetabular components.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
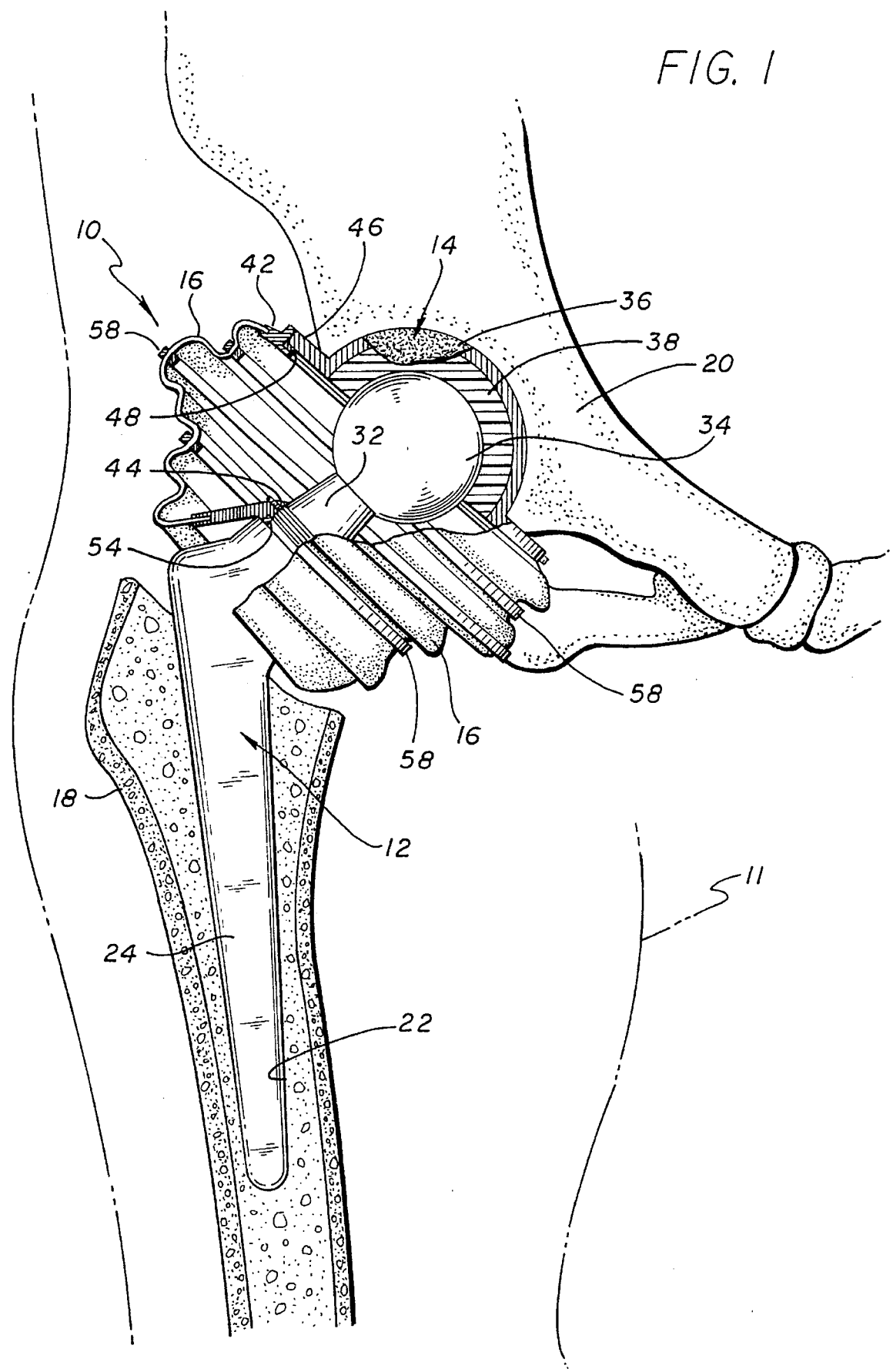
FIG. 1 is a fragmented perspective view, shown in partially in vertical section, and illustrating an improved prosthetic joint embodying the novel features of the invention.

As shown in the exemplary drawings, an improved prosthetic joint referred to generally in FIG. 1 by the reference numeral 10 is provided for implantation into the body of a patient 11. The prosthetic joint 10 comprises a pair of prosthetic components identified generally by reference numerals 12 and 14 and adapted for secure fixation to adjacent bones within the patient's body. The prosthetic components 12, 14 engage each other to define articulating surfaces which are intended to permit natural or substantially natural and preferably full range of motion. In accordance with the invention, the articulating surfaces defined by the prosthetic components 12, 14 are encapsulated within a semipermeable membrane 16.

The prosthetic joint 10 of the present invention is shown in the accompanying drawings in the form of a hip prosthesis. In this regard, the prosthetic component 12 comprises a femoral component adapted for attachment to the upper end of the patient's femur 18, whereas the second prosthetic component 14 comprises an acetabular component adapted for secure attachment to the patient's acetabulum 20. The semipermeable membrane 16 prevents systemic distribution of particulate debris which may be generated at the articulating surfaces as a result of normal mechanical wear of the prosthetic joint. The membrane 16 also prevents migration of other particulate debris, such as particulate associated with the interface between each prosthetic component and adjacent patient bone, to prevent such debris from interfering with the articulating joint surfaces. However, the membrane 16 permits substantially unrestricted circulation of natural body fluids such as serum and synovial fluids to the articulating surfaces for lubrication. Although the invention is shown and described in the context of a hip prosthesis, it will be understood that the semipermeable membrane may be used in combination with other prosthetic joint structures, such as knee joints, shoulder joints and the like.

As shown in FIG. 1, the illustrative hip joint prosthesis includes the femoral component 12 adapted for surgical implantation with and affixation to the upper end of the patient's femur 18. In this regard, in accordance with conventional hip prosthesis installation procedures, the upper end of the femur 18 is surgically resected to expose the medullary canal 22. The femoral component 12 includes an elongated stem 24 having a size and shape for seated and typically press-fit installation into the medullary canal 22. A neck 32 protrudes upwardly from an enlarged upper segment of the femoral component and is adapted to carry a generally spherical or ball-shaped head 34. This femoral component 12, as described, is constructed from a relatively biostable and biocompatible high strength material, such as cobalt-chrome or titanium alloy. The stem 24 is securely fixed to the femur 18 as by use of a known bone cement (not shown) or by means of porous bone ingrowth surfaces (also not shown).

The acetabular component 14 of the prosthesis 10 typically comprises a generally hemispherically shaped outer shell 36 having an external size and shape for seated mounting into the patient's acetabulum 20. Secure affixation of the shell 36, formed typically from a material similar to the femoral component 12, is achieved in a known manner, such as by means of a selected bone cement, porous ingrowth surfaces, or by use of bone screws (not shown).

The cup-shaped acetabular shell 36 receives a press-fitted and generally hemispherically shaped bearing member 38 formed typically from a high density plastic material, such as polyethylene. The bearing member 38 defines an open-sided socket for seated reception of the head 34 on the femoral component 12. Thus, the socket-defining surfaces of the bearing member 38 cooperate with the external surface of the ball-shaped head 34 to define the articulating surfaces for the prosthetic joint 10.

As shown in FIGS. 1–6, the semipermeable membrane 16 has a generally annular or cylindrical shape with a circular cross sectional geometry to surround and thus encapsulate the articulating surfaces of the prosthetic joint. In one preferred form, the semipermeable membrane comprises a medical grade and highly flexible and high tensile strength fabric material such as an expanded polytetrafluoroethylene (ePTFE) of the type marketed by W. L. Gore & Associates of Newark, Del., under the trademark GORE-TEX. This membrane material is suitably attached at one end to the acetabular shell 36, and at the opposite end to the femoral component 12 at a location along the neck 32.

More particularly, the opposite ends of the membrane 16 are securely attached as by a clamped edge-fit connection to a pair of mounting collars 42 and 44. The collar 42 has an internally threaded segment for simple thread-on connection with a male thread 45 (FIGS. 3 and 6) formed on a peripheral rim 46 of the acetabular component 14. A seal ring gasket 48 is compressed between the mounting collar 42 and the rim 46 FIG. 3) when the collar 42 is attached to the acetabular component. At least one and preferably a pair of set screws 50 are carried by the mounting collar 42 to lock the collar in place on the acetabular component when final implantation position is achieved.

Figure 2:
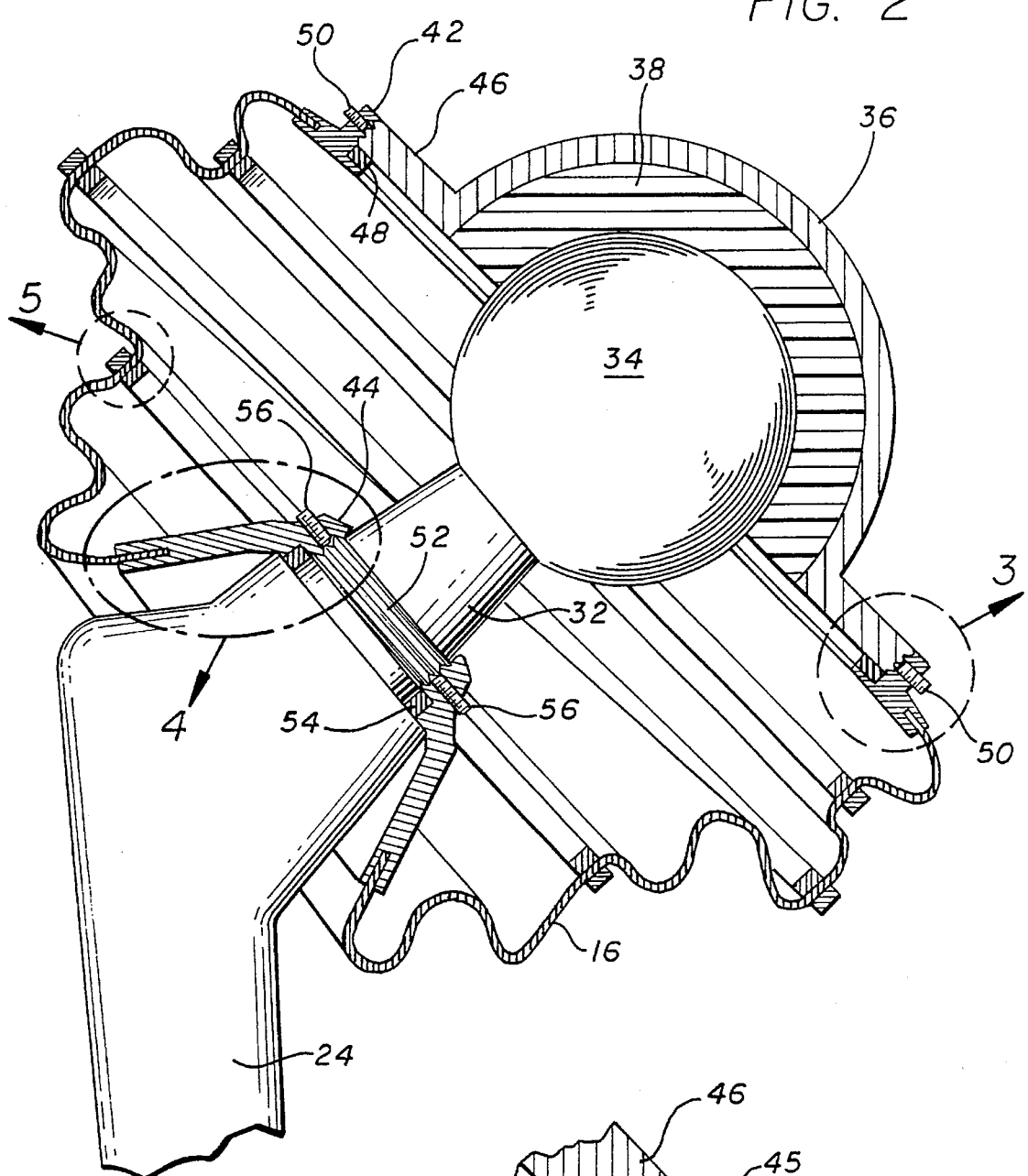
FIG. 2 is an enlarged fragmented perspective view depicting the prosthetic joint of FIG. 1 in more detail.
Figure 3:
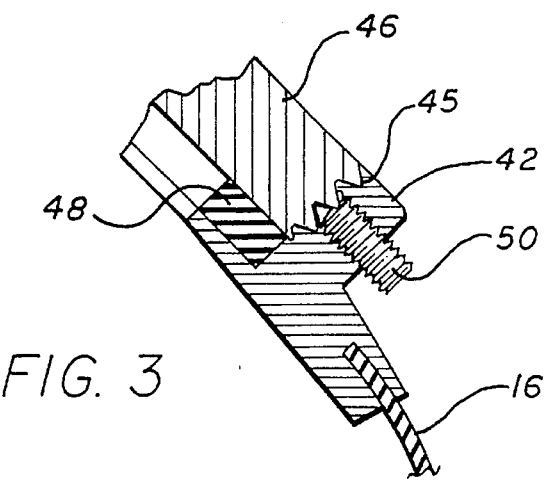
FIG. 3 is an enlarged fragmented sectional view corresponding generally with the encircled region 3 of FIG. 2.
Figure 4:
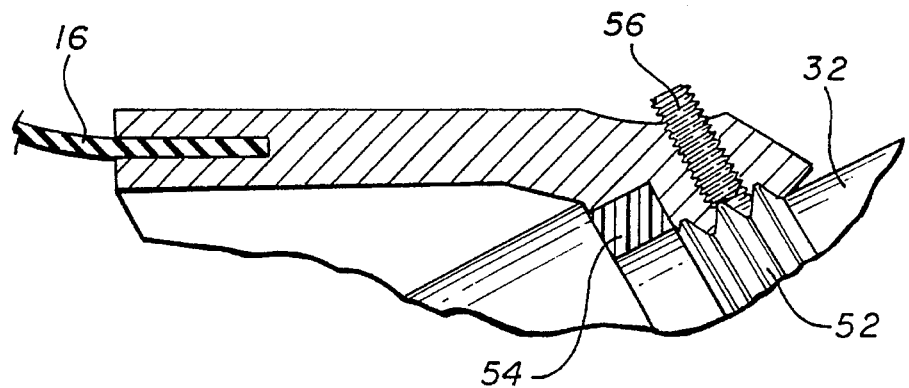
FIG. 4 is an enlarged fragmented sectional view corresponding generally with the encircled region 4 of FIG. 2.
Figure 5:
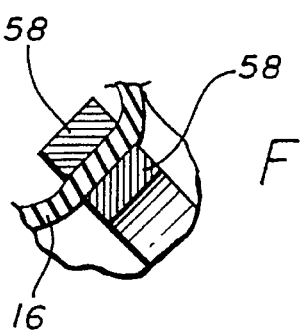
FIG. 5 is an enlarged fragmented sectional view corresponding generally with the encircled region 5 of FIG. 2.
Figure 6:
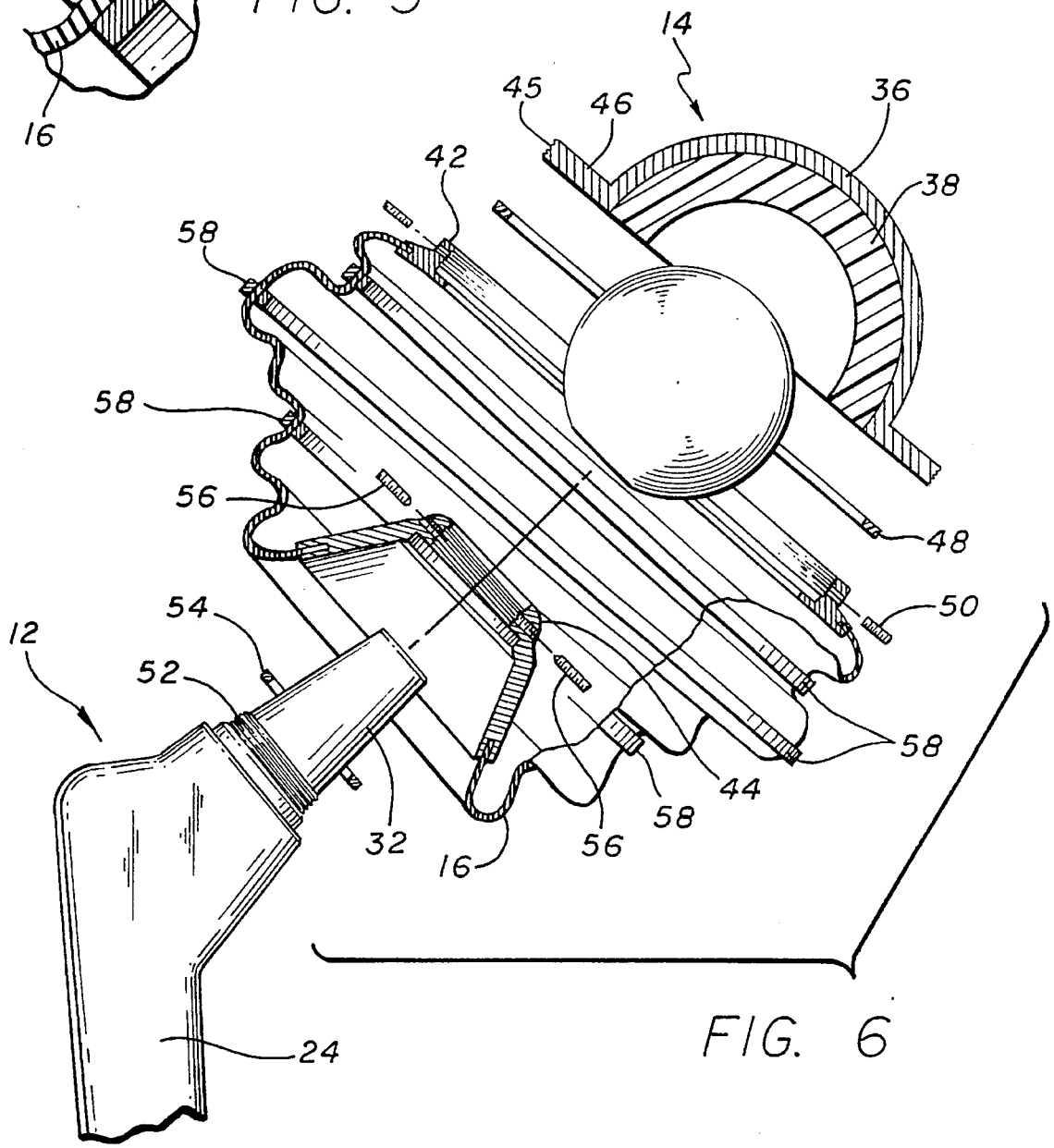
FIG. 6 is a fragmented and exploded perspective view illustrating assembly of the components forming the prosthetic joint.

The second mounting collar 44 has a similar threaded segment for thread-on connector to a male thread 52 on the neck 32 of the femoral component 12 (FIGS. 2, 4 and 6). A seal ring gasket 54 is again provided for compression between the collar 44 and the neck 32 when the mounting collar is installed. The mounting collar 44 also carries at least one and preferably a pair of set screws 56 to lock the collar in place when final implantation position is achieved.

The lower mounting collar 44 on the femoral component 12 has a flared shape extending downwardly and outwardly about the neck 32 (FIGS. 2, 4 and 6). The geometry is chosen to position the flexible membrane away from the articulatory interface between the ball head 34 and the acetabular bearing 38. In this regard, the overall length of the membrane 16 is sufficient to accommodate a normal full range of joint motion, whereby the membrane will be suspended loosely in an irregular lax shape about the prosthetic joint.

A plurality of relatively rigid or nondeformable stay rings 58 are secured to the membrane at selected positions to prevent collapse of the membrane into interference with the articulatory surfaces. Each stay ring 58 is shown as an interfitting pair of hoops disposed in press-fit concentric relation on opposite sides of the membrane 16, and having sufficiently smooth edges to preclude cutting or tearing of the membrane. The distance between each mounting collars 42, 44 and the adjacent stay ring 58 is less than the distance between the articulatory surfaces to the point of membrane attachment to the collar, whereby the membrane cannot flex into interference with the joint motion surfaces. In a preferred geometry, a third stay ring 58 is mounted on the membrane at a position generally equidistant between the rings closest to the two mounting collars 42, 44.

During surgery, the mounting collars 42, 44 and the membrane 16 can be installed and removed as needed to check prosthesis fit. When the surgeon is satisfied that final implantation position has been attained, the set screws can be tightened to lock the membrane 16 in place.

In use, the semipermeable membrane 16 permits substantially unobstructed flow-through circulation of natural body fluids to the articulating surfaces of the prosthetic joint. These body fluids provide substantial and natural lubrication for the articulating surfaces, and thereby minimize mechanical wear. The semipermeable membrane 16 acts as a filter to prevent particulate migration through the membrane in either direction. Thus, plastic-based particulate generated in the course of normal mechanical wear of the articulating surfaces is confined to a chamber or capsule bounded by the membrane 16, thereby preventing systemic distribution of such particulate and potential undesirable medical consequences associated therewith. Other particulate and debris of the type produced typically at an interface between either one of the prosthetic components 12, 14 and patient bone, such as bone fragments, cement fragments and/or particulate from porous ingrowth surfaces, is prevented from migrating to the articulating surfaces of the joint, to prevent high rates of wear which might otherwise be associated therewith.

If desired, the semipermeable membrane may beneficially be preimpregnated with a selected antibiotic at the time of implantation surgery. The presence of this antibiotic can be important to minimize and even present infections which can sometimes occur following surgery.

A variety of further modifications and improvements to the invention described herein will be apparent to those skilled in the art. Accordingly, no limitation on the invention is intended by way of the foregoing description and accompanying drawings, except as set forth in the appended claims.

What is claimed is:

1. A prosthetic joint for implantation into a patient's body, said prosthetic joint comprising:

first and second prosthetic components adapted for fixation respectively to an adjacent pair of patient bones, said first and second prosthetic components having interengageable articulating surfaces;

a generally cylindrical semipermeable flexible membrane; and means for connecting opposite ends of said semipermeable membrane to said first and second prosthetic components so that said membrane surrounds and encapsulates said articulating surfaces to permit a substantially normal range of motion and to avoid interfering with such motion, whereby said membrane permits substantial body fluid circulation therethrough for purposes of lubricating said articulating surfaces while substantially preventing migration of particulate through said membrane; and at least one stay ring carried by said membrane to prevent said membrane from interfering with said articulating surfaces, said at least one stay ring being mounted on said membrane at a position so that the distance along said membrane between said at least one stay ring and the adjacent one of said connecting means is less than the distance between said adjacent one of said connecting means and said articulating surfaces.

2. The prosthetic joint of claim 1 wherein said connecting means comprises a pair of mounting collars at opposite ends of said membrane.

3. The prosthetic joint of claim 2 wherein said mounting collars are adapted for removable mounting respectively onto said first and second prosthetic components.

4. The prosthetic joint of claim 3 wherein said mounting collars are adapted for threaded connection respectively onto said first and second prosthetic components.

5. The prosthetic joint of claim 4 further including means for locking said mounting collars respectively onto said first and second prosthetic components.

6. The prosthetic joint of claim 1 wherein said connecting means further includes seal means for sealed connection of the opposite ends of said membrane to said first and second prosthetic components.

7. The prosthetic joint of claim 1 wherein said first and second prosthetic components respectively comprise a femoral component and an acetabular component of a hip prosthesis.

8. The prosthetic joint of claim 7 wherein said femoral component comprises a femoral stem having an upwardly extending neck with a ball-shaped head mounted thereon, and wherein said acetabular component comprises an outer acetabular shell having a generally cup-shaped bearing liner received therein, said connecting means being for connecting said membrane between said neck and said shell.

9. The prosthetic joint of claim 7 wherein said connecting means adapted for connection of said membrane to said femoral component has a flared shape extending away from said acetabular component.

10. The prosthetic joint of claim 1 wherein said membrane comprises an expanded polytetrafluoroethylene fabric.

11. The prosthetic joint of claim 1 wherein said membrane is impregnated with an antibiotic.

12. The prosthetic joint of claim 1 wherein said at least one stay ring comprises a plurality of stay rings mounted along the length of said membrane, each of said stay rings being mounted at a position so that the distance along said membrane between said stay ring and the adjacent one of said connecting means is less than the distance between said adjacent one of said connecting means and said articulating surfaces.

13. A prosthetic joint for implantation into a patient's body, said prosthetic joint comprising:

first and second prosthetic components adapted for fixation respectively to an adjacent pair of patient bones, said first and second prosthetic components having interengageable articulating surfaces;

a semipermeable flexible membrane of generally cylindrical shape defining open opposite ends;

first connecting means for connecting one end of said membrane to said first prosthetic component;

second connecting means for connecting the other end of said membrane to said second prosthetic component so that said membrane surrounds and encapsulates said articulating surfaces to permit substantially normal range of motion and to avoid interfering with such motion, whereby said membranes permits substantial body fluid circulation therethrough for purposes of lubricating said articulating surfaces while substantially preventing migration of particulate through said membrane; and at least one stay ring carried by said membrane to prevent said membrane from interfering with said articulating surfaces, said at least one stay ring being mounted along the length of said membrane of a position wherein the distance along said membrane between said at least one stay ring and said second mounting means is less than the distance between said second connecting means and said articulating surfaces.

14. The prosthetic joint of claim 13 wherein said first connecting means comprises an annular collar for thread-fit mounting onto said first prosthetic component.

15. The prosthetic joint of claim 14 wherein said second connecting means comprises an annular collar for thread-fit mounting onto said second prosthetic component.

16. The prosthetic joint of claim 13 wherein said first and second prosthetic components respectively comprise a femoral component and an acetabular component of a hip prosthesis.

17. The prosthetic joint of claim 13 wherein said at least one stay ring comprises first and second stay rings mounted along the length of said membrane, said first stay ring being mounted along the length of said membrane at a position wherein the distance between said membrane and said first connecting means is less than the distance between said first connecting means and the articulating surfaces, and said second stay ring being mounted along the length of said membrane at a position wherein the distance between said membrane and said second connecting means is less than the distance between said second connecting means and the articulating surfaces.

18. The prosthetic joint of claim 13 wherein said membrane comprises an expanded polytetrafluoroethylene fabric.

19. The prosthetic joint of claim 13 wherein said membrane is impregnated with an antibiotic.

* * * * *